(12) United States Patent
Hajduk et al.

(10) Patent No.: US 6,605,473 B1
(45) Date of Patent: Aug. 12, 2003

(54) METHOD FOR CHARACTERIZING LIBRARIES OF DIFFERENT MATERIALS USING X-RAY SCATTERING

(75) Inventors: Damian Hajduk, San Jose, CA (US); James Bennett, Santa Clara, CA (US); Rakesh Jain, Cupertino, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 34 days.

(21) Appl. No.: 09/667,119

(22) Filed: Sep. 20, 2000

Related U.S. Application Data (62) Division of application No. 09/215,417, filed on Dec. 18, 1998, now abandoned.

(51) Int. Cl.[7] ............................................... G01N 23/00
(52) U.S. Cl. .......................... 436/174; 378/79; 378/86; 378/208; 422/102; 435/288.4; 435/305.3
(58) Field of Search ....................... 422/102; 435/288.4, 435/309.3; 436/174, 183; 378/79, 86, 208

(56) References Cited

U.S. PATENT DOCUMENTS

| | | | |
|---|---|---|---|
| 3,911,279 A | | 10/1975 | Gilland et al. |
| 4,076,981 A | | 2/1978 | Sparks et al. |
| 4,595,561 A | * | 6/1986 | Thornton et al. |
| 4,682,891 A | * | 7/1987 | de Macario et al. |
| 5,163,078 A | | 11/1992 | Iketaki |
| 5,629,524 A | | 5/1997 | Stettner et al. |
| 5,646,976 A | | 7/1997 | Gutman |
| 5,684,711 A | | 11/1997 | Agrafiotis et al. |
| 5,757,882 A | | 5/1998 | Gutmann |
| 5,776,359 A | | 7/1998 | Schultz et al. |
| 5,976,813 A | * | 11/1999 | Beutel et al. |
| 6,143,496 A | * | 11/2000 | Brown et al. |

FOREIGN PATENT DOCUMENTS

| | | |
|---|---|---|
| DE | 18 22 077 | 11/1999 |
| WO | WO 98/36826 | 8/1988 |
| WO | WO 98/22758 | 8/1995 |
| WO | WO 97/32208 | 9/1997 |
| WO | WO 99/59716 | 11/1999 |

OTHER PUBLICATIONS

Isaacs, E.D. et al., (1998) Appl. Lttr. 73 (13): 1820–1822 Synchrotron X–ray Microbeam Diagnostics of Combinatorial Synthesis.

Weinberg et al. Science, vol. 279 (1998) 837–839.

Cong et al., Angew. Chem. Int. Ed., (1999) 38, No. 4, 483–488.

Franks, A. Brit. J. Appl. Phys. (1958), 9: 349–352 Some developments and applications of microfocus x–ray diffraction techniques.

(List continued on next page.)

Primary Examiner—Jan Ludlow

(57) ABSTRACT

A method for preparing a library is provided in which the library contains an array of elements and each element contains a different combination of materials. A related apparatus includes an x-ray beam directed at the library, a chamber which houses the library and a beamline for directing the x-ray beam onto the library in the chamber. The chamber may include a translation stage that holds the library and that is programmable to change the position of the library relative to the x-ray beam and a controller that controls the movement of the translation stage to expose an element to the x-ray beam in order to rapidly characterize the element in the library. During the characterization, the x-ray beam scatters off of the element and a detector detects the scattered x-ray beam in order to generate characterization data for the element.

3 Claims, 8 Drawing Sheets

OTHER PUBLICATIONS

Milch, J. Appl. Cryst. (1983) 16: 198–203 A Focusing X–ray Camera for Recording Low–Angle Diffraction from Small Specimens.

Gruner, Curr.Op. Struct. Biol. (1994) 4: 765–767 X–ray detectors for macromolecular crystallography.

Gruner, Rev. Sci. Inst. (1989) 60: 1545–1551 CCD and vidicon x–ray detectors: Theory and practice (invited).

Allinson, N. M. Nucl. Inst. Methods Phys. Res. (1989) A275: 587–596 Solid–State Detectors for Synchrotron Radiation Experiments.

Eikenberry et al., in Morgan ed. Photoelectric Image Devices, Bristol: Inst. Of Physics Conf Ser No. 21, Institute of Physics (1992) 273–281. X–ray detectors: comparison of fim, storage phosphors and CCD detectors.

Hajduk, D., Ph.D. Dissertation, Princeton Univ. 1994 Morphological Transitions in Block Copolymer.

International Application No. PCT/US99/3016: Copy of International Preliminary Examination Report dated Mar. 4, 2001.

GADDS –General Area Detector Diffraction System, System Configurations Applications, Analytical X–Ray Systems, Siemens Technologies (1996).

D5000 matic X–Ray Process–Diffractometer, Siemens Automation Group, Siemens Technologies (date unknown).

Platform –Siemens' Advanced Modular Goniometer System, Siemens Industrial Automation, Inc., Analytical Instrumentation, Siemens Technologies (1994).

Hi–Star Area Detector, Siemens Industrial Automation, Inc., Analytical Instrumentation, Siemens Technologies (1996).

Summer 1996 –What's New with General Area Diffraction Systems (GADDS), Siemens Technologies (1996).

Lab Report X–Ray Analysis, Percent Crystallinity in Polymers, Siemens Analytical X–ray Systems, Siemens Technologies (1995).

Lab Report X–Ray, Analysis, Low–Angle Diffraction with Siemens' GADDS System, Siemens Analytical X–ray Systems, Siemens Technologies (1996).

Lab Report X–Ray Analysis, Apparent Crystallite Size of Polymers with Siemens' GADDS System, Siemens Analytical X–ray Systems, Siemens Technologies (1996).

Bruker Advanced X–Ray Solutions, Diffractoin Solutions for Combinatorial Screening–D8 Discover With GADDS, Bruker AXS Inc. (2000).

*DIFFRAC$^{plus}$ X–Ray Diffraction Software*, Siemens Analytical X–ray Systems, Siemens Technologies (1995).

*D5000 X–ray Diffractometer*Siemens Analytical X–ray Systems, Siemens Technologies (date unknown).

Analytical Application Note—Comparison of a Two–Dimensional Position–Sensitive Detector and a Scintillation Detector on Samples with Preferred Orientation, Richard B. Orgega and Kingsley L. Smith, Siemens Analytical X–Ray Instruments, Siemens Technologies, (Jun. 1992).

GADDS/Hi–Star Area Detector Pre–Installation Guide, Siemens Analytical X–ray Systems, Siemens Technologies (1995).

\* cited by examiner

METHOD FOR CHARACTERIZING LIBRARIES OF DIFFERENT MATERIALS USING X-RAY SCATTERING

This application is a divisional application of U.S. patent application Ser. No. 09/215,417, filed Dec. 18, 1998, now abandoned which is incorporated herein by reference, the teachings of which are incorporated herein by reference.

BACKGROUND OF THE INVENTION

This invention relates generally to an apparatus and method for rapidly determining the characteristics of an array of diverse materials which have been created on a surface of a substrate, and in particular, to an apparatus and method for rapidly determining the characteristics of a library of diverse materials using high energy electromagnetic radiation.

Combinatorial material science refers generally to methods for creating a collection of chemically diverse compounds or materials and to methods for rapidly testing or screening this library of compounds or materials for desirable characteristics or properties. The combinatorial technique, which was introduced to the pharmaceutical industry in the late 1980s, has dramatically sped up the drug discovery process. Recently, combinatorial techniques have been applied to the synthesis of inorganic materials. Using various surface deposition techniques, masking strategies or processing conditions, it is possible to generate hundreds or thousands of materials with distinct compositions per square inch in an array of elements which form a library. The materials generated using these combinatorial techniques have included high temperature superconductors, magnetoresistors, phosphors and pigments. The discovery of new catalysts should also benefit from these combinatorial techniques. General combinatorial material science methodologies are disclosed, for example, in U.S. Pat. No. 5,776,359 which is incorporated herein by reference.

The problem is that, although these libraries of hundreds or thousands of new potential materials have been generated, these libraries need to be screened for performance characteristics or properties and conventional screening techniques are not sufficiently fast. Another problem for conventional characterization techniques is the low concentration of components in each element of the library. It is therefore necessary to be able to accurately measure these low concentration levels.

In general, x-ray scattering is a well known characterization technique. In addition, the various pieces of an x-ray scattering apparatus are well known. For example, U.S. Pat. Nos. 5,757,882, 5,646,976 and 5,163,078 describe a multilayer mirror being used in an x-ray beamline. The use of flat glass mirrors for x-ray optics is disclosed in Franks, A., *British Journal of Applied Physics.*, Volume 9, page 349 (1958) and Milch, J. R., *Journal of Applied Cryst.*, Volume 16, page 198 (1983). X-ray beamlines with rotating anode sources and two flat glass mirrors are disclosed in Milch, J. R., *Journal of Applied Cryst.*, Volume 16, page 198 (1983) and Hajduk, D. A., *Morphological Transitions in Block Copolymers*, Ph.D. dissertation, Princeton University (1994). In addition, x-ray detectors, such as multiwire area detectors (See U.S. Pat. Nos. 3,911,279 and 4,076,981) and CCD-based detectors with integral memories (See U.S. Pat. No. 5,629,524) are known. Many x-ray detectors have also been described in various journals and other publications including Gruner, S. M., *Curr. Op. Struct. Biol.* 1994, 4, 765; Gruner, S. M., *Rev. Sci. Inst.* 1989, 60, 1545; Ilinson, N. M., *Nucl. Inst. Methods Phys. Res.* 1989, A275,587; and Eikenberry E. F. et al., "X-Ray Detectors: Comparison of Film, Storage Phosphors and CCD Detectors" in Morgan, ed. *Photoelectric Image Devices* Bristol: Inst. of Physics Conf. Ser. No. 121, Institute of Physics 1992, 273.

One conventional technique for structural characterization is x-ray scattering. In this technique, a monochromatic, collimated x-ray beam illuminates a material of interest, and the spatial distribution of the scattered radiation is analyzed to provide information on the structure, dimensions, and degree of ordering of the specimen. Low concentrations of strongly scattering constituent atoms or substructures may also be detected and quantified by this technique. Similar results may be obtained by analyzing the distribution of photon energies scattered into a fixed region of space from a polychromatic x-ray beam. Although the low photon flux and brilliance to characteristic of commercially available instruments is acceptable for measurements of individual samples, it is of limited value for combinatorial materials science work. Typical measurements on conventional sources require at least fifteen minutes per specimen, implying at least 24 hours to characterize a 96-element library. Obviously, the total screening time will increase dramatically as the total number of elements increases. Therefore, it is desirable to provide an apparatus and method for characterizing libraries of different materials using x-ray scattering to solve the above problems associated with conventional systems and techniques. It is to this end that the present invention is directed.

SUMMARY OF THE INVENTION

An apparatus and method for characterizing a library of different materials using x-ray scattering in accordance with the invention provides numerous advantages over conventional characterization apparatus. For example, compared to conventional instruments, the apparatus advantageously delivers both a higher total photon flux and a higher flux per unit area to each library element. This reduces the time required to analyze each element thereby reducing the total time needed for library characterization. It also reduces the time required for calibration of the instrument as described below. The light generated by such an intense beam when it strikes a phosphorescent screen is easily detected by the eye which facilitates alignment of the instrument prior to the measurement. The apparatus also has a modular sample stage which supports and moves a library containing a plurality of elements so that the plurality of elements may be tested more rapidly than with conventional apparatus. The apparatus in accordance with the invention may perform spatial scanning so that arrays and libraries of materials may be rapidly analyzed and characterized. The positioning of the library in relation to the x-ray beam may be computer controlled so that the apparatus may automatically characterize and analyze each element on the library by moving the library a predetermined distance. This automatic movement of the library relative to the x-ray beam eliminates human error and avoids having a human reposition the library after each element is characterized.

In accordance with another aspect of the invention, a method for preparing a library of materials for characterization and analysis by the x-ray apparatus is provided. The library may be prepared several different ways. In the embodiments below, samples which are powders are being used, but the library preparation method may be used with other types of samples. In a first embodiment, a plate having a predetermined thickness may have an array of holes drilled through the plate. The holes may be sealed at one end with a chemically inert material which is nearly transparent to x-rays of the appropriate wavelength and that does not generate appreciable x-ray scattering in the angular regime of interest. Suitable materials may include poly(imide) (Kapton™), poly(ethylene terephthalate) (Mylar™), thin aluminum foils and thin beryllium foils. Once the different materials have been deposited into the appropriate hole, the open ends of the holes may be sealed with the same material. The library is now ready for characterization using the x-ray apparatus. In a second embodiment, the same metal plate with a first end covered by the plastic material may be used and then the powders to be placed in each hole may be suspended in a non-solvent liquid with a low vapor pressure and deposited in the appropriate holes using a liquid handling robot. During the loading process, the plate may be heated to promote evaporation of the non-solvent liquid and the other end of the holes may be sealed with the same plastic which leaves the powder in the hole for characterization. In a third embodiment, the sample powders may be blended with a viscous, non-solvent binder and each sample may be deposited onto a piece of the plastic film Once the elements are dried, the plastic film may be mounted on an aluminum frame to provide mechanical support and strength to the film which contains the dried elements.

In a fourth embodiment of the library preparation method, the first ends of the holes in the same metal plate are blocked by a sheet of material, and the wells thus formed are filled by a solution of the materials of interest in a volatile solvent. The blocking material is chosen so as to be nonreactive with respect to the solution of interest and to be insoluble in the solvent. The blocking material may therefore include fluorinated polymers such as Teflon™, poly(imide) or metals. The solvent is removed by air drying, by vacuum drying or by exposure to an oxygen-free environment followed by gentle heating in a vacuum. Once of the solvent has been removed, the remaining materials of interest may form a film which completely fills and remains in each wells so that the blocking material may be removed. If the remaining materials of interest do not form a film with sufficient mechanical strength to remain in the wells when the blocking material is removed, the blocking material must be made from a material that is substantially transparent to x-rays as described above. Suitable materials may include poly(imide) (Kapton™), poly(ethylene terephthalate) (Mylar™), thin aluminum foils and thin beryllium foils.

Thus, in accordance with the invention, an apparatus for characterizing a library is provided in which the library contains an array of elements, each element contains either a chemically distinct combinations of materials, or a chemical composition which may be identical to that existing elsewhere on the library but has been subject to distinct processing conditions. The apparatus comprises an x-ray beam directed at the library, a chamber which houses the library, and a beamline for directing the x-ray beam to illuminate a region on the library in the chamber. The chamber further comprises a translation stage that holds the library and that is programmable to change the position of the library relative to the x-ray beam and a controller that controls the movement of the translation stage to expose each element to the x-ray beam in order to rapidly characterize each element in the library.

In accordance with another aspect of the invention, a method for characterizing a library is provided in which the library contains an array of elements, each element contains either a chemically distinct combinations of materials, or a chemical composition which may be identical to that existing elsewhere on the library but has been subject to distinct processing conditions. The method comprises directing an x-ray beam generated by an x-ray source towards the library housed within a chamber and moving the library in a predetermined manner to expose each element of the library separately to the x-ray beam in order to rapidly characterize each element in the library.

In accordance with another aspect of the invention, an apparatus for characterizing a library is provided in which the library contains an array of elements and each element contains either a chemically distinct combinations of materials, or a chemical composition which may be identical to that existing elsewhere on the library but has been subject to distinct processing conditions. The apparatus comprises means for generating an x-ray beam which is directed towards the library, a chamber which houses the library and means for directing the x-ray beam onto the library in the chamber. The chamber further comprises means for holding the library, means for changing the position of the library relative to the x-ray beam and means for controlling the movement of the translation stage to expose each element to the x-ray beam in order to rapidly characterize each element in the library.

In accordance with yet another aspect of the invention, a method for preparing a library is provided in which the library contains an array of elements and each element contains either a chemically distinct combinations of materials, or a chemical composition which may be identical to that existing elsewhere on the library but has been subject to distinct processing conditions. The method comprises forming an array of holes from a first side of a plate through to a second side of the plate, sealing a first side of the plate with a film to form wells in the plate, depositing a predetermined amount of one or more materials into each well of the plate, and sealing the second side of the plate with a second piece of film to trap the deposited one or materials in each of the wells in the plate so that a beam may impinge upon each element containing the one or materials and characterize the elements of the library.

In accordance with yet another aspect of the invention, a method for preparing a library is provided in which the library contains an array of elements and each element contains either a chemically distinct combinations of materials, or a chemical composition which may be identical to that existing elsewhere on the library but has been subject to distinct processing conditions. The method comprises forming one or more deposition compounds, each deposition compound comprising one or more materials blended into a viscous, non-solvent liquid, depositing the deposition compounds onto a sheet of film at predetermined locations to form an array of elements, drying the deposition compounds onto the film to form a library of one or more materials, and mounting the firm with the dried deposition compounds onto a frame to provide support to the plastic film so that the deposition compounds may be rapidly characterized.

In accordance with still another aspect of the invention a method for preparing a library is provided in which the library contains an array of elements and each element contains either a chemically distinct combinations of materials, or a chemical composition which may be identical to that existing elsewhere on the library but has been subject to distinct processing conditions. The method comprises blocking the first ends of holes in a metal plate with a sheet of material so that the wells thus formed are filled by a solution of the materials of interest in a volatile solvent. The blocking material is chosen so as to be nonreactive with respect to the solution of interest and to be insoluble in the solvent. The solvent is then removed by air drying, by vacuum drying or by exposure to an oxygen-free environment followed by gentle heating in a vacuum. Once of the solvent has been removed, the remaining materials of interest may form a film which completely fills and remains in each wells so that the blocking material may be removed. If the remaining materials of interest do not form a film with sufficient mechanical strength to remain in the wells when the blocking material is removed, the blocking material must be made from a material that is substantially transparent to x-rays as described above.

DETAILED DESCRIPTION OF A PREFERRED EMBODIMENT

The invention is particularly applicable to an apparatus and method for characterizing a library of materials in powder form using x-ray scattering and it is in this context that the invention will be described. It will be appreciated, however, that the apparatus and method in accordance with the invention has greater utility because it may be used to characterize other materials.

An x-ray characterization apparatus and method in accordance with the invention may provide various advantages over conventional characterization apparatus. For example, the apparatus in accordance with the invention significantly reduces the total amount of time typically necessary to characterize a library of materials since the apparatus reduces the time needed to analyze each element of the library. The apparatus also advantageously delivers more energy flux to the surface of the library which reduces the time each element must be exposed to the x-ray beam. The apparatus also has a modular sample stage which supports and moves the library so that the elements of the library may be tested more rapidly than with a conventional apparatus. The apparatus in accordance with the invention may perform spatial scanning so that arrays and libraries of materials may be rapidly analyzed and characterized. The positioning of the library in relation to the x-ray beam may be computer controlled so that the apparatus may automatically characterize and analyze each element of the library by moving the library a predetermined distance. This automatic movement of the library relative to the x-ray beam eliminates human error and avoids having a human slowly re-position the library after each element is characterized. Now, an x-ray characterization apparatus in accordance with the invention will be described.

Figure 1:
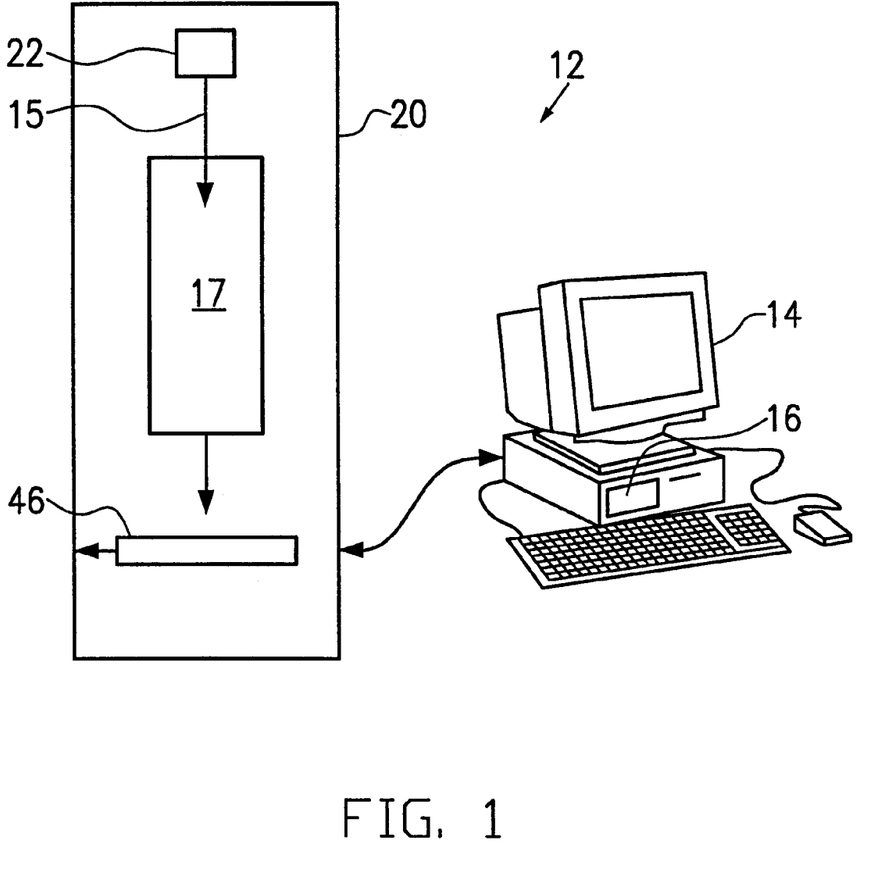
FIG. 1 is a block diagram illustrating an x-ray characterization apparatus in accordance with the invention.

FIG. 1 is a block diagram illustrating an x-ray characterization system 12 in accordance with the invention which may include a computer system 14 and an x-ray characterization apparatus 20. The computer system may be a personal computer or any other type computer system. The computer system 14 may control the operation of the x-ray characterization apparatus 20 including the opening or closing of a servomechanically controlled safety shutter as described below, the positioning of an element in a library 46 as described below in front of an x-ray beam 15, receiving the scattering image data from the x-ray characterization apparatus 20 and processing the scattered image data. The positioning of the library 46 and the reception and processing of the scattering image data may be performed by a software application 16 which may be stored in the computer system and executed by a microprocessor (not shown) contained in the computer system. The software application may be one or more pieces of code. Thus, the software may, for example, automatically properly position each element in the library in front of the x-ray beam so that each element may be characterized rapidly.

In operation, the x-ray characterization apparatus 20 generates an x-ray beam 15 which is directed by a beamline 17 towards an element of the library 46. The x-ray beam is then scattered by the element which it strikes. The individual photons scattered may be detected and a position of each photons in a X-Y mesh of wires of a multiwire detector may be determined. The multiwire detector may be preferably used due to the high speed at which data may be transferred from the detector to the computer system. However, instead of the multiwire detector, other x-ray detectors known to those skilled in the art, such as a CCD detector or storage phosphors (also known as image plates) may also be used to detect the scattered photons. The output of the detector for each scattering may be sent to the computer system 14. Once the characterization of an element has been completed, the software application 16 may automatically move the library to expose another element in the library 46 to the x-ray beam and generate scattering data for that element. In this fashion, each element in the library is automatically positioned in front of the x-ray beam 15 and characterized. Thus, the speed with which a library containing a plurality of elements may be characterized is greatly increased. Now, more details of the x-ray characterization apparatus 20, which may include a transmission mode embodiment as shown in FIG. 2A and a reflective mode embodiment shown in FIG. 2B, will be described.

Figure 2A:
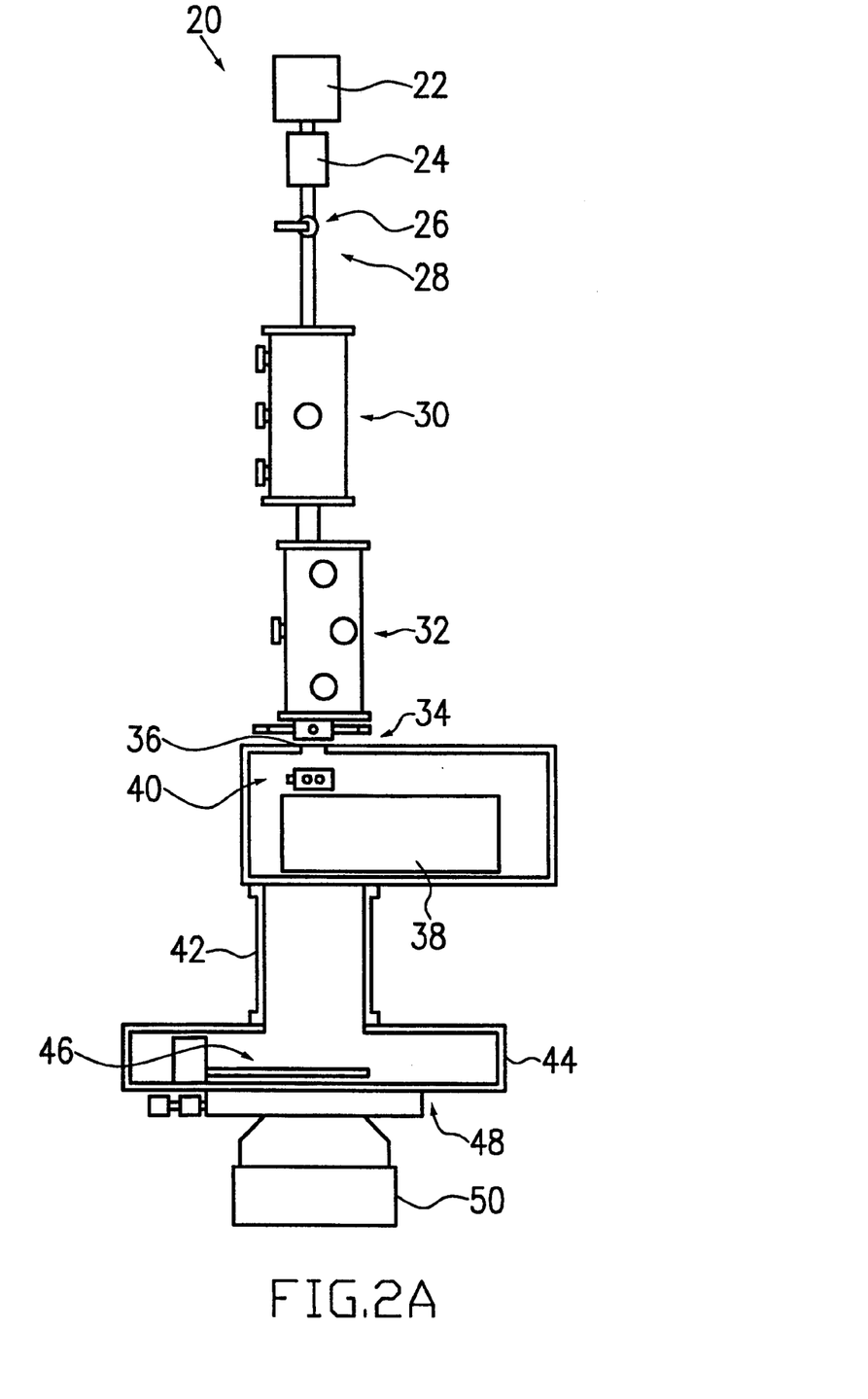
FIG. 2A is a diagram illustrating more details of a transmission mode x-ray characterization apparatus in accordance with the invention.

FIG. 2A is a diagram illustrating an embodiment of the x-ray characterization apparatus in accordance with the invention. This embodiment is a transmission mode embodiment in which the generated x-rays may pass through the elements in the library and the scattered energy may be recorded by a detector behind the library as described below. The x-ray characterization apparatus 20 may include a source 22 of intense x-ray radiation, an optional multi-layer mirror 24, a safety shutter 26, a foil 28, a vertical focusing mirror 30, a horizontal focusing mirror 32, a set of primary slits 34, a set of windows coated with a film 36, an optional first chamber 38, a set of parasitic slits 40, a flight tube 42, a combinatorial sample chamber 44 in which a library 46 may be characterized using the intense x-ray beam, a beamstop translation assembly 48 and a x-ray detector 50. Each of these elements of the x-ray characterization apparatus will now be described in more detail.

The intense x-ray radiation source 22 may generate a beam of x-rays which are directed towards the library 46 in order to scatter the x-ray off of (reflection mode) or through (transmissive mode) an element in the library. In a preferred embodiment, the intense x-ray radiation source 22 may be a rotating anode x-ray generator, such as a Rigaku RU-200BH model, which may include a microfocus point focus cathode and a copper target. As is well known, an electron beam is generated by passing an electric current through a tungsten filament and then accelerating the resulting free electrons through a potential difference of 40 kV to produce 60 mA of beam current. The x-ray radiation may be focused to illuminate a predetermined spot size, such as 0.2×2 mm, on the target surface, which may be foreshortened to 0.2×0.2 mm when viewed along the beam axis. This generates a broad spectrum of x-rays comprised of a number of discrete x-ray lines superimposed on a broad background.

In another embodiment of the invention, a synchrotron may be used as the source of the intense x-ray radiation. Although synchrotron source are capable of much higher photon fluxes and brilliances than can be obtained with laboratory sources (fixed anode or rotating anode x-ray generators), such devices are considerably more complex and expensive than laboratory sources. The high fluxes associated with a synchrotron also places severe constraints on the performance of the associated x-ray detectors, requiring detectors of greater cost and complexity as well.

The radiation may exit the shielded enclosure of the source 22 through a beryllium window in the wall of the generator and may pass through a window made of a material substantially transparent to x-rays, such as Kapton™, into the multi-layer mirror 24. The multi-layer mirror is an optional element which may be removed from the apparatus 20. The mirror may be oriented so that it meets the Bragg criterion for the copper $K\alpha$ wavelength (1.54 Å) which compose a majority of the total x-ray output by the source 22 and the multi-layer thickness is varied along the length of the mirror to convert the diverging radiation beam from the source 22 into a parallel, nearly monochromatic beam. To minimize absorption or scattering of the x-ray radiation, the multi-layer mirror chamber may be filled with helium gas. In a preferred embodiment, the multi-layer mirror may be a multi-layer mirror manufactured by Osmic Corp. of Troy, Mich.

To avoid accidents, the x-ray generator 22 may have a servomechanically actuated lead shutter immediately after the beryllium window which blocks the beam when it is not in use. To provide further backup to the shutter in the generator 22, the apparatus may include a mechanical shutter 26. The output from the shutter, if open, is then passed through the foil 28. The material of the foil may be selected to exhibit preferential absorption for photons with energies higher than a desired energy which further monochromaticizes the beam. For the copper $K\alpha$ radiation being used, the foil may be made out of nickel. If other x-ray target materials such as molybdenum are used, then a different foil material may be used.

Once the beam passes through the foil, it strikes the vertical focusing mirror 30 and the horizontal focusing mirror 32, each of which may be a well-known Franks mirror. The focusing mirrors 30, 32 may be a grazing incident mirror constructed from two float glass flats coated with a thin layer of nickel and oriented so as to reflect x-rays with wavelengths equal to or greater than the $K\alpha$ wavelength. Thus, higher energy photons pass through both of the mirrors. The mirrors, by means of a bending press, may each be curved so as to focus the parallel beam from the multi-layer mirror 24 to a point at the location of the detector 50. To minimize unwanted absorption and scattering of the x-ray beams, the vertical and horizontal focusing mirrors 30, 32 may be maintained in a helium atmosphere.

Once the beam passes through the vertical and horizontal focusing mirrors 30, 32, the beam passes through the set of primary slits 34 which helps to determine the exact dimensions of the beam striking the elements on the library and to block unwanted unreflected radiation which may be present. At this point, the x-ray beam exits the optical beam line which is helium filled, as described above, through the set of windows 36 made from a nearly transparent material, such as Kapton™, for example, into the optional first chamber 38 which may have a vacuum applied to it. In this apparatus, the first chamber is not used for a sample since this chamber can only contain a single sample. Therefore, instead of the first chamber 38, a flight tube may replace the first chamber. If the first chamber is used, the beam may strike a set of parasitic slits 40, located about 10 cm downstream from the set of primary slits 34, which eliminate any parasitic scattering caused by the set of primary slits. When the flight tube is used instead, the parasitic slits may be mounted at the end of the flight tube.

For the characterization measurements in accordance with the invention, the flight tube 42 may be attached to the first chamber if the first chamber is used. The flight tube may be a predetermined length, such as 50 cm, which is chosen such that radiation scattered through the angle(s) of interest strikes the detector with sufficient lateral separation from the transmitted radiation so as to distinguish between transmitted photons and scattered photons. The angles are dictated by the wavelength of the incident x-rays and the dimensions of the scattering features within the sample. The flight tube may be manufactured out of aluminum and may have a vacuum applied. The flight tube may serve as an evacuated beampath for the transmitted and scattered radiation when the first chamber 38 is being used for characterizing a single sample. The back end of the flight tube 42 may be connected to the combinatorial sample chamber 44 to form a continuous evacuated beampath.

As the intense x-ray beam passes through the combinatorial sample chamber 44, the beam passes through or reflects off of an element in the library positioned in front of the beam, as described below. The transmitted, scattered and reflected radiation exits the combinatorial sample chamber 44. In the transmissive embodiment of the invention, the radiation transmitted through the element may be blocked by the beamstop translation assembly 48 which may be a lead disk mounted on a strip of material, such as Mylar™. The material is attached to a two-axis translation system which permits the location of the beamstop to be adjusted (i.e., behind the element currently being characterized) while the combinatorial sample chamber 44 is kept vacuated. The radiation scattered off of the element in the library may then be detected by the detector 50. In a preferred embodiment, the detector 50 may be Seimens HI-STAR multiwire area detector. Now, the combinatorial sample chamber 44 will be described in more detail with additional details being provided below.

The combinatorial sample chamber 44 may be attached to an optical rail on which the detector is also placed so that the position of the library 46 in the combinatorial sample chamber 44 relative to the detector 50 may be adjusted. In particular, for elements with small features and therefore large scattering angles, the library may be closer to the detector (approximately 1–4 cm), while for a element with larger features and therefore smaller scattering angles, the library may be 1–2 m from the detector.

The combinatorial sample chamber 44 may permit a variety of different environmental characteristics to be changed so that the effects of changes in the environmental characteristics on the elements may be measured. For example, the combinatorial sample chamber 44 may be pressurized to a positive pressure or a vacuum to determine, for example, the effects of a determined time at a particular pressure on the library or even on a particular element. In this case, additional pressure-tight nearly transparent windows may be mounted at the apertures where the x-rays enter and exit the chamber 44. As another example, an electric or magnetic field may be applied to one or more elements in the library as described in co-pending U.S. patent application Ser. No. 09/174,986, filed Oct. 19, 1998 on behalf of the same assignee as this patent and which is incorporated herein by reference. In addition, some form of mechanical stress, such as shear stress or stretching stress, may be applied to the library. The temperature or the gases within the combinatorial sample chamber 44 may also be changed to determine the effects of different temperature or gases on the elements. Finally, to look at the thermal changes of a element, such as a catalyst, each element in the library may include an embedded thermal sensor and heater.

Within the combinatorial sample chamber 44, there may be two orthogonally mounted linear translation stages, as described below. A frame attached to one of the translation stages, as described below, may accept a library containing a plurality of elements or elements, such as ninety-six elements in a preferred embodiment. The samples or elements may be powders, solutions, suspensions or films deposited or transparent substrates as will be described below with reference to FIGS. 11 and 12. In the transmissive embodiment shown in FIG. 2, the frame is oriented by the translation stages to be normal to the x-ray beam so that some fraction of the incident photons are scattered our of the main beam as it passes through the library element. To position the stages, a pair of computer-controlled motors, such as stepper motors, may be used as described below. The stepper motors may be controlled by the software application 16 shown in FIG. 1. In one embodiment of the invention, closed-loop motor control may be used. In another embodiment, no closed-loop motor control is used so that the software application 16 directs each motor to step an appropriate number of times in the desired direction to obtain the desired displacement from the starting point to a particular point at which a particular element is in front of the x-ray beam.

To calibrate the x-ray characterization apparatus 20 to characterize elements of the library, a radioactive source may be installed on the frame which normally holds the library at the proper spatial location so the focused x-ray beam passes through the radioactive source. The characteristics of the detector are then determined as specified by well-known procedures. Next, the radioactive source is removed and a second frame containing a calibrant powder is installed. The calibrant powder may be supplied by the National Institute of Standards and Technology (NIST) and may be lanthanum hexaborate (d=4.157 Å). The scattering from this calibrant powder may be used to determine the library-to-detector distance needed for subsequent measurements.

During the characterization of each element in a library, the various commands needed to acquire and process the data for each element in the library may be written into a text file which may be read by the detector as is well known. Once a library is inserted into the frame, the translation stages may be moved so that the x-ray beam passes through a first element. The x-ray safety shutter may then be opened and the first scattering image is recorded. The translation stage control software may then move the library to bring the next element of the library into the path of the x-ray beam. After recording the second image, the library is moved to the next element. While the library is being moved, which takes several seconds, the detector may process and save the image. The computer controlling the detector and the computer software controlling the motors may or may not communicate with each other. If the software application do communicate with each other, then the next exposure may proceed as soon as the library is properly positioned. In this manner, each element in the library may be characterized.

During the processing of the scattering data, which may occur in the detector or in the computer system, various operation may occur. For example, the raw scattering data may be corrected for detector response characteristics, such as spatial distortion or non-uniform sensitivity. This correction may be followed by a determination of the total number of counter (crossings of the detector wires) as a function of scattering angle ($2\theta$) over a fixed range of azimuthal angles ($\chi$) Now, a reflective mode embodiment of the x-ray characterization apparatus 20 in accordance with the invention will be described.

Figure 2B:
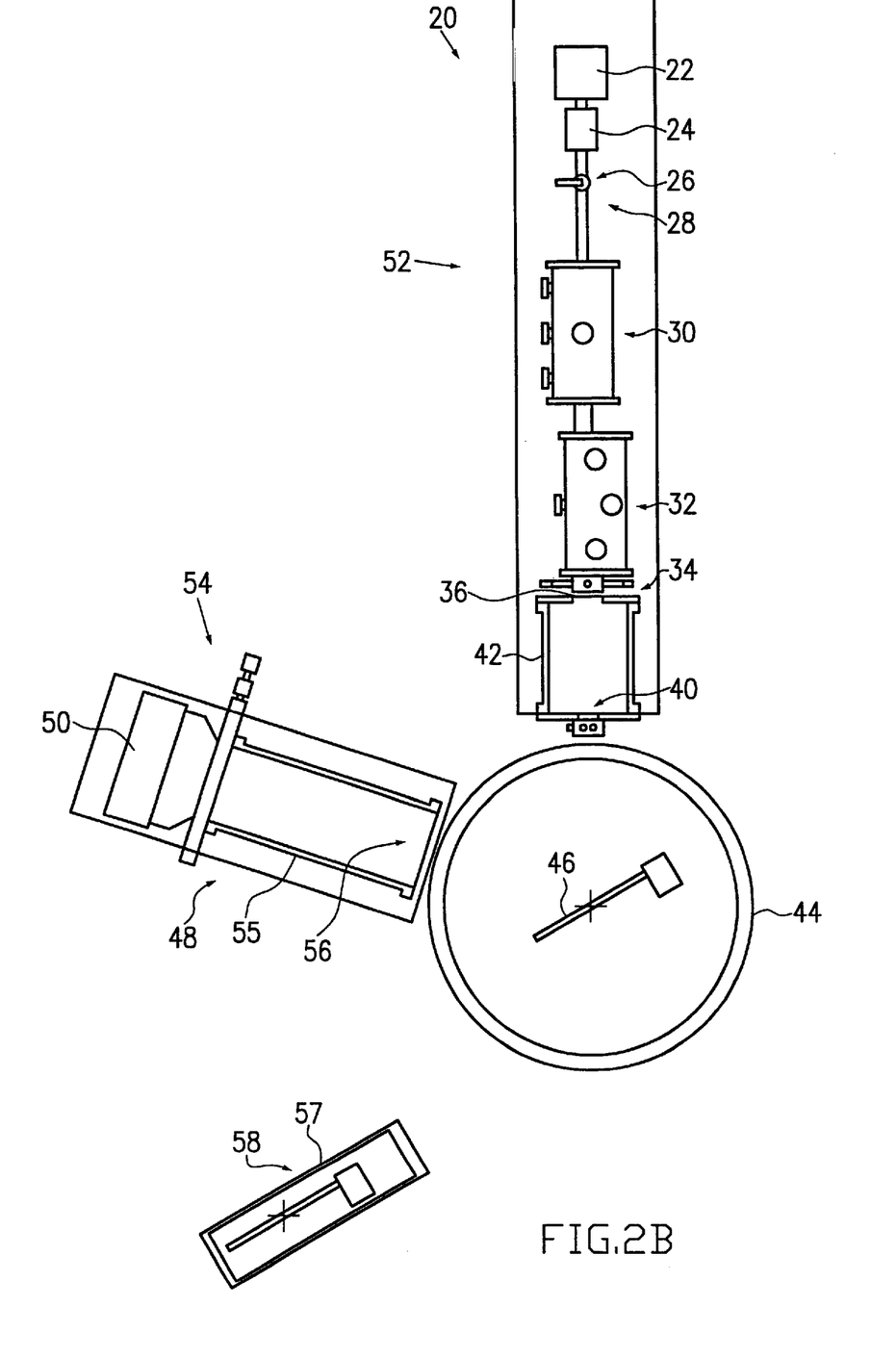
FIG. 2B is a diagram illustrating more details of a reflective mode x-ray characterization apparatus in accordance with the invention.

FIG. 2B is a diagram illustrating a reflective mode embodiment of the x-ray characterization apparatus 20 in accordance with the invention. For the description of this embodiment, many parts are similar to the transmission mode apparatus described above and these parts will not be described here in any detail. Thus, the reflective mode apparatus 20 may include the intense x-ray source 22, the optional multi-layer mirror 24, the safety shutter 26, the foil 28, the first and second sets of focusing mirrors 30, 32, the primary slits 34, the window 36, the flight tube 42 and the set of parasitic slits 40. In this embodiment, however, one end of the flight tube 42 is connected to the second set of focusing mirrors 32 and the parasitic slits 40 are connected to the other end of the flight tube 42 since the library 46 and the combinatorial sample chamber 44 are now separate from the rest of a beamline so that the beamline and the detector 50 may rotate relative to the library 46 as will be described below. In particular, for the reflective embodiment of the apparatus, a beamline 52 and a detector assembly 54 may be rotated about a fixed combinatorial sample chamber 44. Therefore, the beamline 52 and the detector assembly 54 may each be connected to a typical rotation stage arm (not shown) to permit the beamline 52 and detector assembly 54 to be rotated relative to the library 46. Thus, the positions of the beamline and detector may be adjusted to the proper reflection angle to detect the x-rays reflected off of the library.

The beamline 52 has the same elements as described above and performs the same function of generating an intense focused x-ray beam and directing it towards the library 46. The detector assembly 54 in this embodiment may include the beamstop assembly 48, the detector 50, a flight tube 55 and a window 56 through which the scattered x-ray beams may enter the detector assembly. In this embodiment, there may be an alternate combinatorial sample chamber 57 which may be used for large scattering angles. The alternate combinatorial sample chamber 57 may include a window 58 through which the x-rays may pass. The combinatorial sample chamber 44 may have a cylindrical shape and may be filled with helium gas to reduce unwanted scattering. As above, the combinatorial sample chamber 44 may have a mechanism, as described below with reference to FIGS. 4 and 5, to position the library in the proper position. As above, the positioning of the library may be computer controlled. Now, an example of a library will be described.

Figure 3:
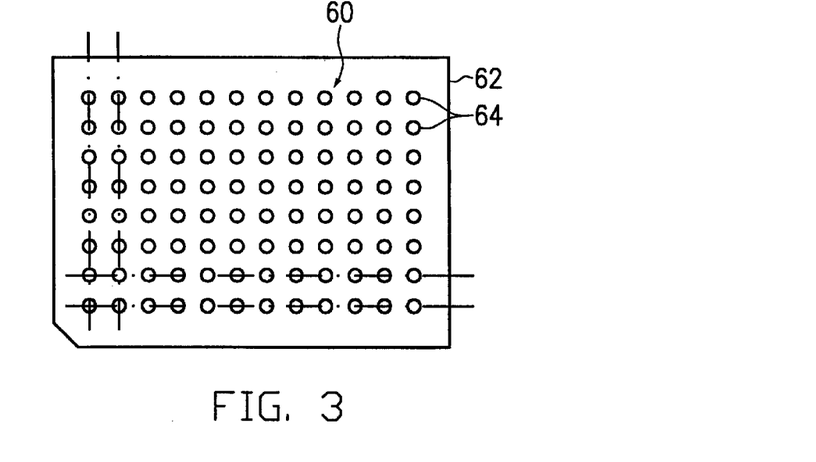
FIG. 3 is a diagram illustrating an example of a library.

FIG. 3 is a diagram illustrating an example of a library 60. The library may be mounted onto the frame to characterize each element in the library. The library may comprise a plate 62, which may be made of a metallic material such as aluminum, having a predetermined thickness, such as ⅛", and a plurality of holes 64 through the plate in a predetermined pattern. In this example, the holes may be drilled through the plate, may be in a rectangular, two-dimensional array pattern, and there may be a total of ninety-six elements in the library. For each hole in the plate, there may be a sample deposited within and sealed into the hole so that the x-ray beam may characterize the characteristics of the sample. The library 60 in accordance with the invention may have other shapes and more or less elements than shown in FIG. 3. Several different embodiments for preparing a library in accordance with the invention will be described below with reference to FIGS. 10A, 10B and 11. Now, more details of the translation stages in accordance with the invention will be described.

Figure 4:
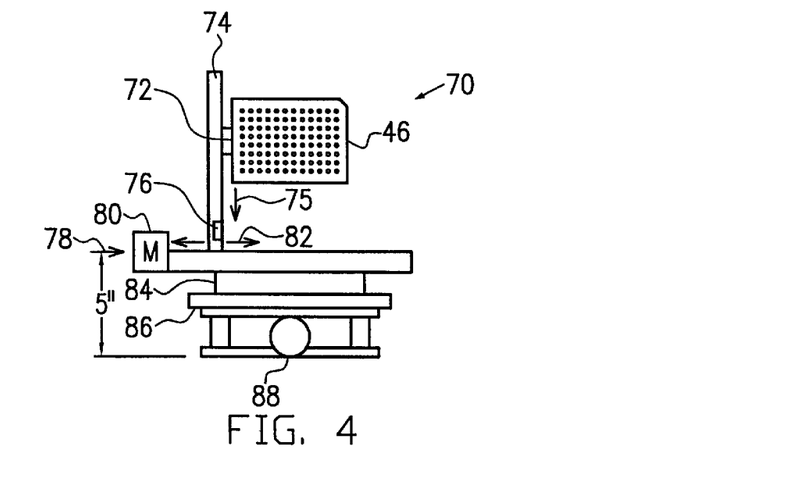
FIG. 4 is a side view of the translation stages in accordance with the invention.
Figure 5:
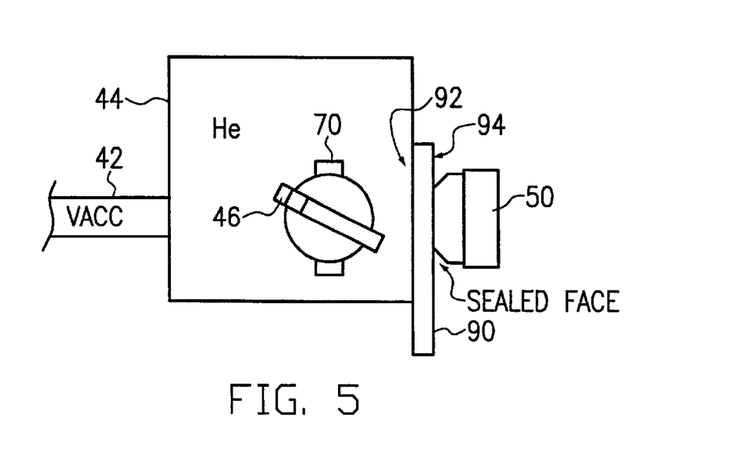
FIG. 5 is a top view of the translation stages shown in FIG. 4.

FIGS. 4 and 5 are a side view and top view, respectively, of translation stages located within the combinatorial sample chamber 44 in accordance with the invention. As shown in FIG. 5, within the combinatorial sample chamber 44 may be a library holder assembly 70 which positions the library 46 relative to the x-ray beam entering the combinatorial sample chamber 44 from the flight tube 42. The combinatorial sample chamber 44 may be attached to the detector 50 which detects the scattering of the x-rays off of the elements in the elements of the library. The position of the detector 50 may be adjusted relative to the position of the library as described below.

The library holder assembly 70, as shown in FIG. 4, may include a pair of rails 72 which hold the library 46. The rails 72 may be attached to a first positioning assembly 74. The first positioning assembly 74 may permit the library to move back and forth along a first axis 75 using a motor 76, such as a stepper motor, which may be controlled by the software application being executed by the computer system as shown in FIG. 1. The first positioning assembly 74 may be connected to a second positioning assembly 78 which may include a stepper motor 80 which moves the library back and forth along a second axis 82. The second positioning assembly 78 may also be controlled by the software application being executed by the computer system as shown in FIG. 1. Thus, using the computer controlled first and second positioning assemblies 74, 78, the library 46 may be automatically positioned so that each element of the library may be characterized using the x-ray beam which increases the speed with which the library may be characterized. The order in which the elements of the library are actually analyzed is not critical to the invention. The library holder assembly 70 may also include a system 84 for rotating the library, and a first and second manual positioning assemblies 86, 88, such as laboratory jacks, for positioning the combinatorial sample chamber during initial installation and calibration.

Figures 6, 7:
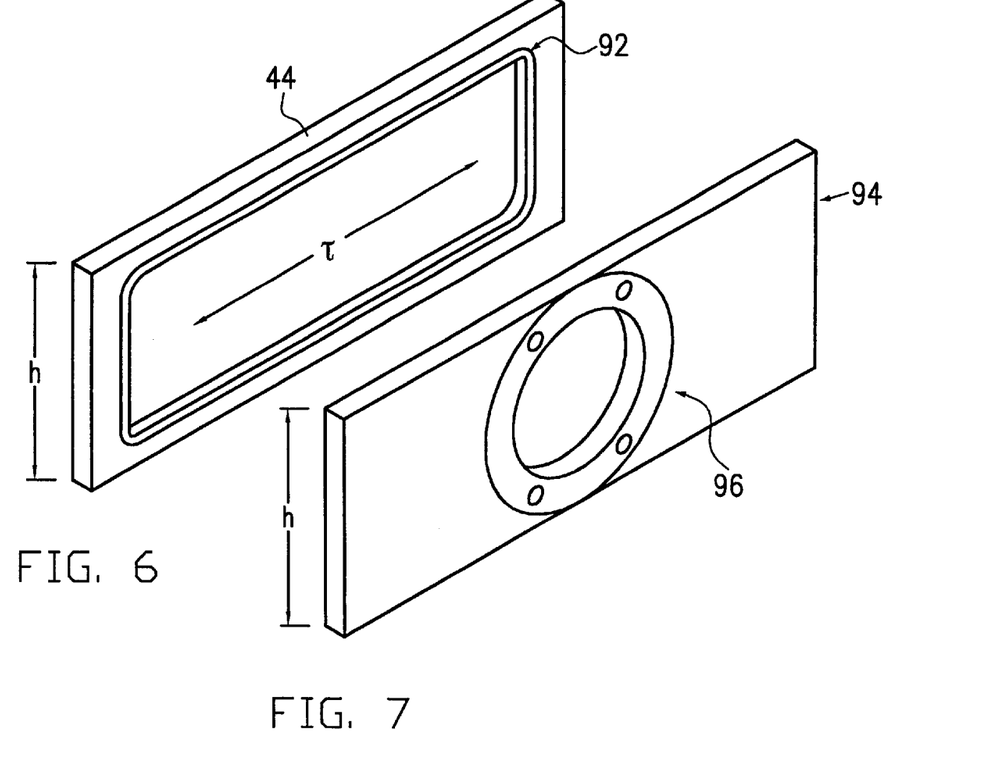
FIGS. 6 and 7 are diagrams illustrating the sealing plates which connect the combinatorial sample chamber to the detector.

To adjust the position of the detector 50 relative to the library 46, the detector may be mounted on a sliding plate mechanism 90. As shown in FIGS. 6 and 7, the sliding plate mechanism 90 may include a seal 92, such as an O-ring, on the outer surface of the combinatorial sample chamber 44 and a sealing plate 94 attached to the face of the detector. The sealing plate 94 may include a seal 96, such as an O-ring, which seals the sealing plate 94 to the detector 50. Thus, the detector 50 and the sealing plate 94 may be moved relative to the combinatorial sample chamber 44 and the seal 92 along a direction τ. When the detector 50 is properly positioned, the sealing plate 94 may be clamped to the wall of the combinatorial sample chamber 44 so that the seal 92 forms an air-tight seal between the combinatorial sample chamber 44, the detector and the sealing plate. Now, the details of an embodiment of-the rails 72 which hold the library will be described briefly.

Figure 8:
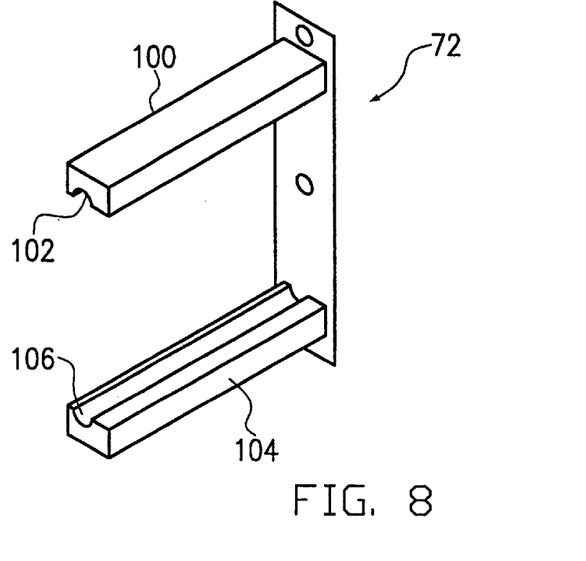
FIG. 8 is a block diagram illustrating more details of the library holder in accordance with the invention.

FIG. 8 is a block diagram illustrating an embodiment of the rails 72 which hold the library. In this embodiment, the rails 72 may include a first rail 100 with a channel 102 at its center and a second rail 104 with a channel 106 at its center so that a library may slide between the rails 100, 104 in the channels 102, 106 and be supported by the rails during the characterization of the elements in the library. Now, the method for controlling the x-ray characterization apparatus will be described.

Figure 9:
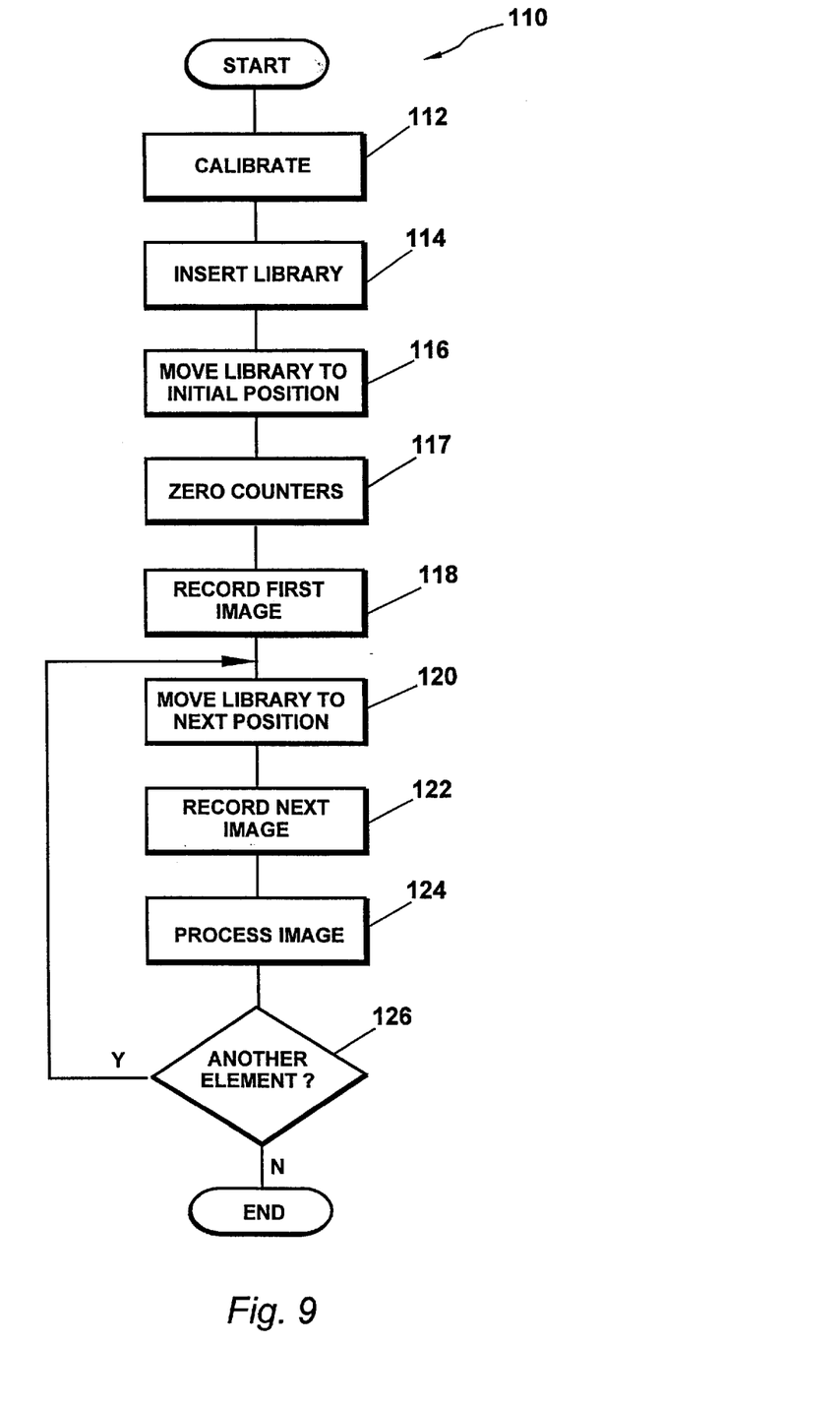
FIG. 9 is a flowchart illustrating a method for controlling the x-ray characterization apparatus in accordance with the invention.

FIG. 9 is a flowchart illustrating a method 110 for controlling the x-ray characterization apparatus in accordance with the invention to rapidly characterize each element in a library. In step 112, the x-ray apparatus may be calibrated as described above. Once the apparatus is calibrated, a library may be inserted into the rails of the library holder mechanism in step 114. At this point, the first and second positioning assemblies are activated in order to move the library to the position as commanded by the software application executed on the computer system in order to characterize each element in the library rapidly. Thus, in step 116, the first and second positioning assemblies are commanded to take a certain predetermined number of steps to place the library in an initial position in which a first element of the library is aligned with the x-ray beam. Next, in step 117, the counters associated with the motors are zeroed since this embodiment of the invention does not use closed loop feedback so that each movement of the motors is from an origin which is set to the initial element of the library. Once the library is positioned in the first position, the safety shutter may be removed and the scattering image generated in step 118 when the x-ray beam passes through the first element is recorded by the detector. For most libraries, this first element may be a calibration element. Once the image for the first element is processed and recorded, the software application commands the stepper motors in the first and second positioning assemblies to step a predetermined number of steps, in step 120, to position the library so that the next element in the library may be characterized. In accordance with another embodiment of the invention in which only selected elements of the library may be characterized, a list of elements and their positions may be provided to the motor controller which then moves the library to the appropriate locations to expose the selected library elements. In one embodiment of the invention, which does not use closed loop feedback techniques, each motor is commanded to step a predetermined number of times from the origin to position the library properly based on information about the library and the position of each element in the library previously generated and available to the software application. The invention may also operate with a closed loop feedback system in which the motors may be commanded to perform a predetermined number of steps and then any error in the positioning may be corrected.

Once the library has been positioned so that next element may be exposed to the x-ray beam, the element is exposed to the x-ray beam in step 122 and an image of the scattering is generated by the detector. In step 124, the detector may process the image as described above and store the image in a memory which may be in the computer system or in the detector. While the detector is processing the image, the software application may determine if there is another element to be characterized in step 126, and loop back to step 120 and command the stepper motors to move the library so that the next element is exposed to the x-ray beam. In this manner, the processing of the image by the detector and the movement of the first and second positioning assemblies to a next element may occur simultaneously which reduces the total time to characterize each element in the library. In one embodiment of the invention, the detector does not communicate with the software application so that the total time to characterize each element is limited to the slowest step (i.e., either the processing or the movement of the stepper motors). In another embodiment of the invention, the detector and software application may communicate with each other so that, as soon as the processing of the image and the movement of the stepper motors is completed, the next element may be characterized which may further reduce the total time necessary to characterize each element in the library. When each element in the library has been characterized the method has been completed.

In addition to serially characterizing each element in a library, the x-ray apparatus may also be controlled by the software application so that the user of the x-ray apparatus may select to characterize any individual element, a group of elements, etc. of the library by simply specifying the library element(s) to be characterized using a simple user interface screen which permits the user to select one or more elements in the library from a graphical representation of the library. For example, once the particular elements are specified by the user, the software application may automatically determine the appropriate number of steps for the first and second positioning assemblies to take in order to position the library to bring the selected element into the x-ray beam. In this manner, the user of the apparatus may determine the elements of interest in the library and the apparatus automatically positions the library which greatly increases the speed with which the characterization of element(s) in the library may occur. The software also permits individual elements of the library to be independently addressable. Now, another embodiment of the characterization method in which the detector computer running the software that controls the detector and the motor controller computer running the software which controls the motors that move the library are separate computer systems will be described in which more details of the method are provided.

In the embodiment of the invention where the detector computer and the motor controller computer are separate, the general steps performed are similar, but the details are different since the two computer systems do not communicate with each other. Thus, in this embodiment, after recording all of the detector correction files as specified by the detector manufacturer and calibrating the sample-to-detector distance, the library is placed in the library holder, and positioned so that the x-ray beam passes through the upper left element of the library (typically denoted by A1). The library position counters may then be zeroed, as described above, to indicate to the motor controller computer that the library is positioned in the initial position. Using a user interface at the motor controller computer, the user may specify the library elements to be analyzed, the exposure time to be used for each element, and the manner in which the two-dimensional images are to be reduced to a one-dimensional profile of counts as a function of position. The motor controller may then generate a list of the position of each element(s) chosen, and a script (e.g., a list of instructions) which is transferred to the detector computer.

The data collection begins when the detector computer is directed to start reading commands from the script. At the same time, the motor computer software is placed into a program mode which locks out manual control of the motor position. In this mode, the motor computer waits for a signal from the detector computer to step to the next element in the position list. Once that signal is received, the motor computer steps the horizontal and vertical motors to the appropriate amount to bring the next element into the x-ray beam.

For each element, the detector computer integrates the photons received by the x-ray detector for a preset time period. Once the image collection is complete, the detector computer signals the motor computer to move to the next element. While the motor computer is executing this translation of the library, the next image is corrected for detector response characteristics, written to a hard disk and collapsed into a one-dimensional format which is also written to disk. The detector assumes that the translation of the library is complete at this point (which is appropriate due to the motor's rate of speed) and immediately starts acquiring the next image. Once the motor computer steps to the last element in the position list, it returns to "normal" mode in which the motors may be operated by the user.

In the preferred embodiment described with reference to FIG. 9, the detector computer and the motor controller computer are preferably one computer system running a software application to handle the detector control and rung another software application which controls the motors so that the two processes may communicate with each other. In addition, in the preferred embodiment, the detector controller and the motor controller may signal each other so that the motor controller may indicate to the detector controller that the library is appropriately positioned so that the next image may be generated and stored by the detector.

Thus, in accordance with the invention, an entire library, a portion of a library or a single element in the library may be rapidly positioned and characterized. With a conventional characterization apparatus, an element in a ninety-six element library may require approximately 15 minutes to characterize while the characterization of the entire library may require at least 24 hours to complete. With the x-ray apparatus in accordance with the invention, however, each element may take approximately 3 minutes to characterize so that the entire library may be characterized in approximately 2.5 hours. The increase in the characterization speed of the library is due to several factors.

First, the x-ray source in accordance with the invention generates an x-ray beam which is more intense (directs more flux to the library) than the conventional x-ray apparatus. The greater intensity x-rays means a reduced exposure time for each library element. A conventional x-ray apparatus and associated optics typically generate a beam containing on the order of 10,000 photons per second while the x-ray apparatus in accordance with the invention may generate at least 6 million photons per second. The intensity of the x-ray beam is increased due to a stronger x-ray source and a better beamline which reduces unwanted scattering and ensures the focused x-ray beam arrives at the library.

The increase in the characterization speed of the x-ray apparatus in accordance with the invention is also due to the first and second positioning assemblies in combination with the software application which permit the library to be rapidly and automatically positioned to characterize each element of the library rapidly. Now, several embodiments of methods for preparing a library that may be used with the x-ray apparatus will be described.

Figure 10A:
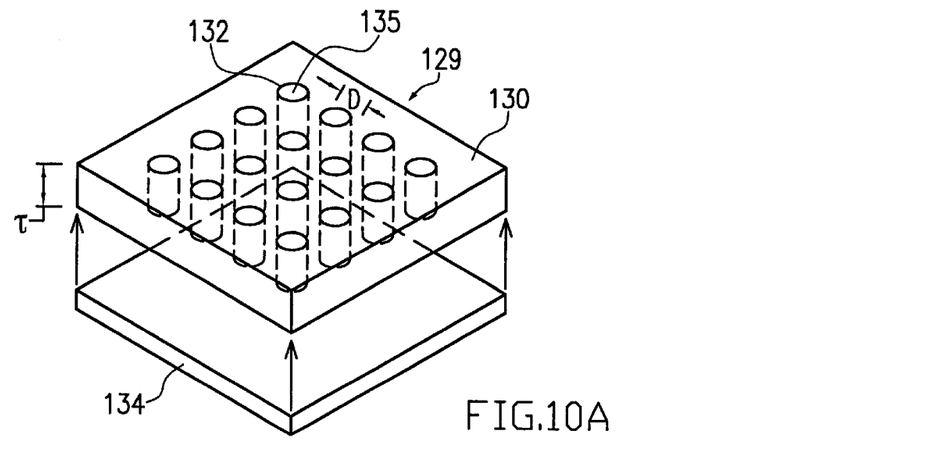
FIGS. 10A and B are diagrams illustrating a first and second embodiments of a method for preparing a library in accordance with the invention.
Figure 10B:
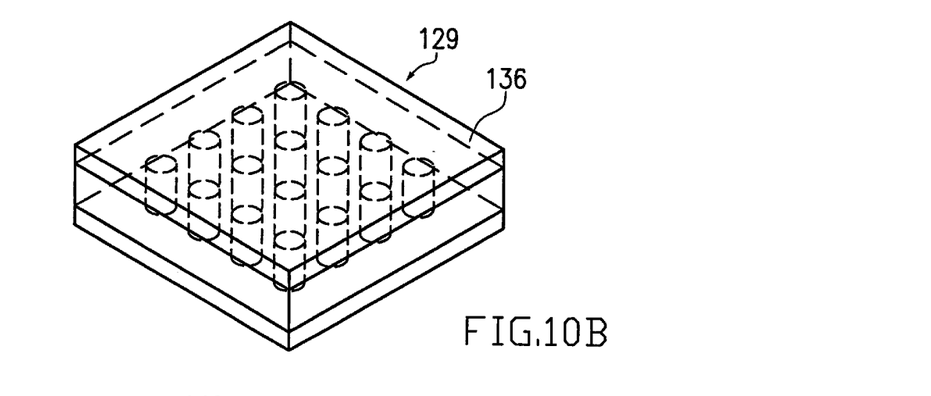

FIGS. 10A and 10B are diagrams illustrating first and second embodiments of a method for preparing a library in accordance with the invention. As shown in FIG. 10A, a library 129 may include a plate 130, which may be manufactured out of a material sufficiently strong to support the library. For example, the plate may be made from a metallic material such as aluminum. The plate may have a predetermined pattern of holes 132 formed through the plate. The holes may be formed, for example, by drilling the holes through the plate. In the example shown, a rectangular array of holes is shown. Once the holes are formed, a piece of adhesive tape or film 134 may be attached to the back surface of the plate as shown by the arrow in FIG. 10A to form a predetermined pattern of wells into which samples 135 may be deposited so that the elements may be characterized. The film 134 may be translucent and/or may permit the x-rays which impinge upon the sample in the well to pass through the film. In a preferred embodiment of the invention, the adhesive film may be Kapton™.

In one embodiment, once dry samples 135 have been manually or automatically deposited in each well, a second film 136, as shown in FIG. 10B, may be placed on top of the plate 130 to seal the samples into their individual wells in the plate. The second piece of adhesive film/tape may be translucent and/or may permit the x-rays which impinge upon the sample in the well to pass through the film and may preferably be Kapton™. The prepared library 129 in accordance with this embodiment of the invention is shown in FIG. 10B.

In accordance with a second embodiment of the invention, each sample may be mixed with a non-solvent liquid and then the combination of the liquid and dry sample may be deposited in each well of the library using a liquid dispensing robot. Prior to the second film 136 being applied to the plate to seal the samples, the plate and sampled-may be heated to evaporate the liquid. Once the liquid is evaporated, the second film may be applied to the plate. The end result of this second embodiment is the same library shown in FIG. 10B. Now, a third embodiment of the method for preparing a library will be described.

Figure 11:
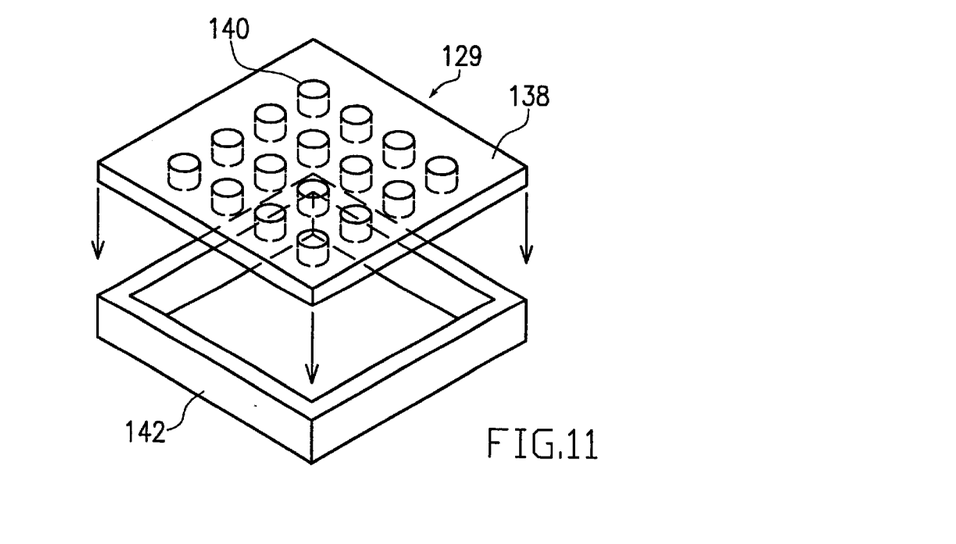
FIG. 11 is a diagram illustrating a third embodiment of a method for preparing a library in accordance with the invention.

FIG. 11 is a diagram illustrating a third embodiment of a method for preparing a library 129 in accordance with the invention. In this embodiment, a film 138, which may be translucent and/or permit x-rays to pass through the adhesive film, such as Kapton™, may be used as a base for the preparation of the library. In particular, a plurality of samples 140 to be included in the library may be mixed with a non-solvent liquid and then deposited on the film in a predetermined pattern similar to the pattern formed by the holes in the plate in the above embodiments. The samples may be deposited by typical semiconductor deposition techniques. Once the deposited samples are dried, a frame 142 may be attached to the side of the film opposite of the samples to support the film and elements during characterization by the x-ray beam. In accordance with all of these embodiments, a library 129 is prepared which may be inserted into the x-ray characterization apparatus in accordance with the invention. Now, an example showing the preparation of a pigment library will be briefly described.

To prepare a library containing pigments, the pigment samples are synthesized on commercially available polypropylene filter plates. After the synthesis is complete and the library is dried, the solid at the bottom of each well is crushed using a 96-pin tool for a 96 element library. Once the samples are crushed, a 96-well aluminum plate, which has a film attached to its back surface, may be placed on top of the filter plate. The assembly may then be inverted and shaken to load the library contents into the wells in the aluminum plate. The aluminum plate may then be covered with an adhesive tape, such as Kapton™, to seal the contents into each well in the aluminum plate. The preparation of the pigment library has now been completed.

In addition to the embodiments of the x-ray apparatus described above, the x-ray apparatus may also use a well known synchrotron to generate the intense x-rays. When using the synchrotron, a more intense x-ray beam is generated so that the exposure time for each element in the library is further reduced to about 1–2 seconds per element. To capture the scattered x-rays generated by the synchrotron, however, a typical multiwire detector used in the prior embodiments is too slow so that a specialized multiwire detector, or an integrating detector, such as a charge coupled device (CCD), may be used. Now, two examples of the results obtained using the x-ray characterization apparatus will be described.

Figure 12:
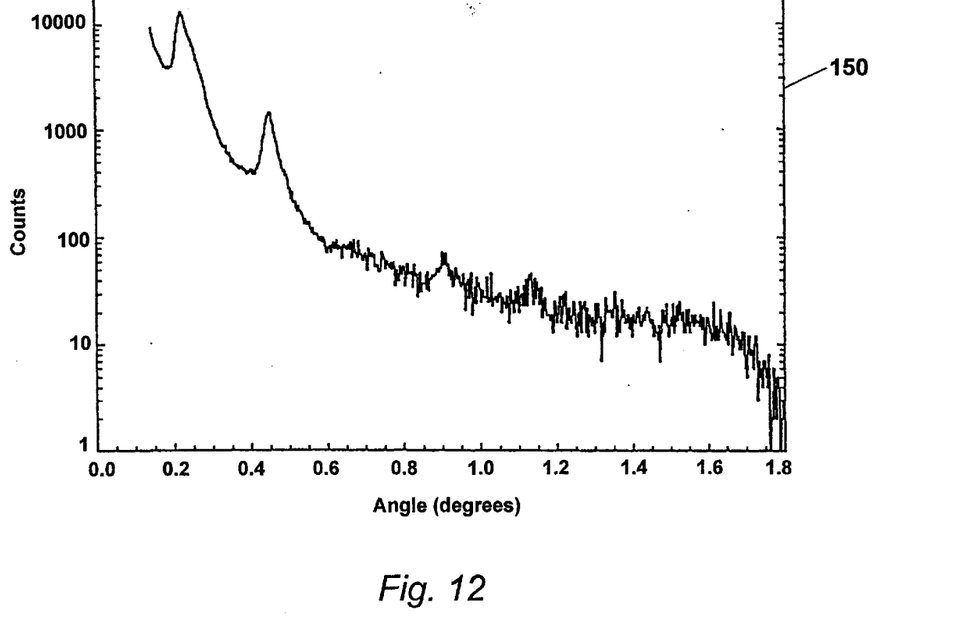
FIG. 12 is a graph showing an example of the results obtained using the x-ray characterization apparatus to characterize block copolymers.

FIG. 12 is a graph 150 showing an example of the results obtained using the x-ray characterization apparatus to characterize block copolymers. In particular, the data in the graph is recorded from a film of commercially available poly(styrene)-poly(butadiene) block copolymer obtained from Aldrich Chemical Co. (catalog number 43,249-0) containing 30% by weight styrene and characterized as received. A 0.125" thick aluminum sample plate containing $3/32$" diameter holes arranged in an 8×12 array was used for this measurement. One face of the plate was compressed against a Teflon™ substrate such that one end of the holes was blocked which formed wells in the plate. Each well was initially filled with approximately 50 ul of a concentrated solution (approximately 25% by weight) of this polymer in toluene. The plate was then dried in a fume hood at ambient temperature, pressure and oxygen content for approximately one hour. 20 ul of the concentrated polymer solution was then added to each well and the drying process was repeated. This process was repeated until each well was filled with the solid polymer.

Any residual solvent was then removed by drying the plate and the Teflon™ backing in a vacuum atmosphere for 24 hours at room temperature, followed by a slow heating to 135 C and subsequent annealing in vacuum at that temperature for 48 hours. At this point, after slow cooling to room temperature, the plate was returned to atmospheric pressure and the Teflon™ backing was removed. For these samples, an x-ray exposure minimum time of 10 seconds at rotating anode power settings of 40 kV accelerating voltage and 60 mA of beam current was used. An exposure time of 300 seconds was used in the representative image, recorded from element A5 of the plate, in order to obtain higher order diffraction data. The reflections appear at angular position ratios of 1:2:4:5 which is characteristic of the alternating layers of polystyrene and polybutadiene. Although no sample-to-detector calibration was recorded for these data, prior calibration indicates that this distance is approximately 205 cm. Assuming this value leads to the angular values shown on the x-axis; the peak positions the correspond to an interlayer spacing of approximately 40 nm. Now, a second example of the results obtained using the x-ray characterization apparatus to characterize a pigment library will be described.

Figure 13:
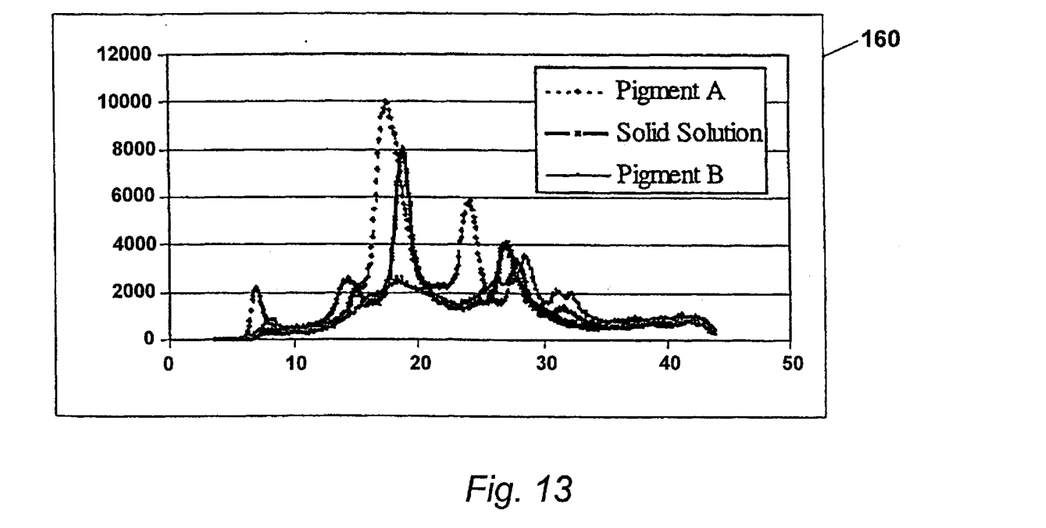
FIG. 13 is a graph illustrating an example of the results obtained using the x-ray characterization apparatus to characterize a pigment library.

FIG. 13 is a graph 160 illustrating an example of the results obtained using the x-ray characterization apparatus to characterize a library of pigment powders. The library was prepared by the preparation method outlined above. An integration time of 60 seconds was used for each element in the library and the sample-to-detector distance was calibrated using the known spacing of lanthanum hexaborate prior to the measurement. In the graph, three traces are shown, one for a solid solution of two pigments, and one for each of the component pigments (A and B). The scattering of the solid solution, based on the results displayed in the graph, is not given by a linear combination of the scatterings for the two components since the former exhibits several peaks (at 6.8, 24.1, 31.0 and 32.3 degrees) that do not appear in the traces for either component.

While the foregoing has been with reference to a particular embodiment of the invention, it will be appreciated by those skilled in the art that changes in this embodiment may be made without departing from the principles and spirit of the invention, the scope of which is defined by the appended claims.

What is claimed is:

1. A method for preparing a library to be characterized using an x-ray apparatus, the library containing an array of elements, each element containing a different combination of materials, the method comprising:

forming an array of holes from a first side of a plate through to a second side of the plate;

sealing a first side of the plate with an x-ray transmissive film to form wells in the plate;

depositing a predetermined amount of one or more materials into each well of the plate; and sealing the second side of the plate with a second piece of x-ray transmissive film to trap the deposited one or more materials in each of the wells in the plate so that an x-ray beam may pass through the films and impinge upon the one or more materials and characterize the one or more materials.

2. The method of claim 1, wherein the depositing comprises depositing a liquid having one or more materials suspended in a non-solvent liquid into each well and heating the plate to evaporate the non-solvent liquid from each well to form a sample in each well.

3. A method for preparing a library to be characterized using an x-ray apparatus, the library containing an array of elements, each element containing a different combination of materials, the method comprising:

forming one or more deposition compounds, each deposition compound comprising one or more materials blended into a viscous, non-solvent liquid;

depositing the deposition compounds onto a sheet of x-ray transmissive film at predetermined locations to form an array;

drying the deposition compounds onto the x-ray transmissive film to form a library of one or more materials; and mounting the x-ray transmissive film with the dried deposition compounds onto a frame to provide support to the x-ray transmissive film so that an x-ray beam may pass through the film and impinge upon the one or more materials and characterize the one or more materials.

* * * * *